United States Patent
Yuan et al.

(10) Patent No.: US 12,020,436 B2
(45) Date of Patent: Jun. 25, 2024

(54) UNSUPERVISED DOMAIN ADAPTIVE MODEL FOR 3D PROSTATE ZONAL SEGMENTATION

(71) Applicant: City University of Hong Kong, Hong Kong (HK)

(72) Inventors: Yixuan Yuan, Hong Kong (HK); Xiaoqing Guo, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 387 days.

(21) Appl. No.: 17/542,535

(22) Filed: Dec. 6, 2021

(65) Prior Publication Data

US 2023/0177692 A1 Jun. 8, 2023

(51) Int. Cl.
*G06T 7/11* (2017.01)
*G06N 3/04* (2023.01)
(Continued)

(52) U.S. Cl.
CPC .................. *G06T 7/11* (2017.01); *G06N 3/04* (2013.01); *G06V 10/431* (2022.01);
(Continued)

(58) Field of Classification Search
CPC ............. G06T 7/11; G06T 2207/10088; G06T 2207/20081; G06T 2207/20084;
(Continued)

(56) References Cited

U.S. PATENT DOCUMENTS 9,025,841 B2  5/2015 Wels et al.
9,269,156 B2  2/2016 Birkbeck et al.
(Continued)

FOREIGN PATENT DOCUMENTS

WO  2018156778 A1  8/2018

OTHER PUBLICATIONS

Simpson, Amber L., et al. "A large annotated medical image dataset for the development and evaluation of segmentation algorithms" arXiv preprint arXiv:1902.09063 (2019).
(Continued)

*Primary Examiner* — Nancy Bitar
*Assistant Examiner* — Dustin Bilodeau
(74) *Attorney, Agent, or Firm* — IDEA Intellectual Limited; Margaret A. Burke; Sam T. Yip (57) ABSTRACT

The present invention provides an unsupervised domain adaptive segmentation network comprises a feature extractor configured for extracting features from a 3D MRI scan image; a decorrelation and whitening module configured for preforming decorrelation and whitening transformation on the extracted features to obtain whitened features; a domain-specific feature translation module configured for translating domain-specific features from a source domain into a target domain for adapting the unsupervised domain adaptive network to the target domain; and a classifier configured for projecting the whitened features into a zonal segmentation prediction. By implementing the domain-specific feature translation module for transferring the knowledge learned from the labeled source domain data to unlabeled target domain data, domain gap between the source and target data can be narrowed. Therefore, the unsupervised domain adaptive segmentation network trained with labeled open-source prostate zonal segmentation dataset (source data) can perform in the target domain without performance degradation.

7 Claims, 5 Drawing Sheets

(51) Int. Cl.
G06V 10/42 (2022.01)
G06V 10/764 (2022.01)
G06V 10/82 (2022.01)
G16H 30/40 (2018.01)

(52) U.S. Cl.
CPC ............ *G06V 10/764* (2022.01); *G06V 10/82* (2022.01); *G16H 30/40* (2018.01); *G06T 2207/10088* (2013.01); *G06T 2207/20081* (2013.01); *G06T 2207/20084* (2013.01); *G06T 2207/30081* (2013.01); *G06V 2201/03* (2022.01)

(58) Field of Classification Search
CPC . G06T 2207/30081; G06T 7/143; G06N 3/04; G06N 3/0455; G06N 3/0464; G06N 3/088; G06N 3/096; G06V 10/431; G06V 10/764; G06V 10/82; G06V 2201/03; G06V 20/64; G16H 30/40; G16H 40/67; G16H 50/70; G16H 50/20
See application file for complete search history.

(56) References Cited

U.S. PATENT DOCUMENTS

2019/0370965 A1* 12/2019 Lay ........................ G06N 20/00
2021/0182687 A1* 6/2021 Son ........................ G06F 18/22
2021/0312615 A1* 10/2021 Yu ......................... G06T 7/0012

OTHER PUBLICATIONS

Clark K, et al. "The Cancer Imaging Archive (TCIA): Maintaining and Operating a Public Information Repository." Journal of Digital Imaging (2013), vol. 26, No. 6, pp. 1045-1057.

Litjens, Geert, et al. "Computer-aided detection of prostate cancer in MRI" IEEE transactions on medical imaging 33.5 (2014): 1083-1092.

Meyer, Anneke, et al. "Towards patient-individual PI-Rads v2 sector map: CNN for automatic segmentation of prostatic zones from T2-weighted MRI." 2019 IEEE 16th International Symposium on Biomedical Imaging (ISBI 2019). IEEE, 2019, p. 696-700.

Guo, Xiaoqing, et al. "Meta Correction: Domain-aware Meta Loss Correction for Unsupervised Domain Adaptation in Semantic Segmentation" Proceedings of the IEEE/CVF Conference on Computer Vision and Pattern Recognition. 2021, p. 1-10.

Meyer, Anneke, et al. "Domain adaptation for segmentation of critical structures for prostate cancer therapy" Scientific reports 11.1 (2021): 1-14.

Van Sloun, Ruud JG, et al. "Deep learning for real-time, automatic, and scanner-adapted prostate (zone) segmentation of transrectal ultrasound, for example, magnetic resonance imaging-transrectal ultrasound fusion prostate biopsy" European urology focus (2019), p. 1-8.

* cited by examiner

UNSUPERVISED DOMAIN ADAPTIVE MODEL FOR 3D PROSTATE ZONAL SEGMENTATION

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention generally relates to automatic prostate zonal segmentation, more specifically, a deep learning method for automatic prostate zonal segmentation based on three dimensional (3D) convolutional neural networks.

BACKGROUND OF THE INVENTION

Prostate zonal segmentation on magnetic resonance imaging (MRI) scan image aims to outline the peripheral zone (PZ) and transition zone (TZ), which is an essential step to provide quantitative assessment of pathomorphology for prostate cancer diagnosis, treatment planning and disease prognosis. In clinical, prostate zonal segmentation is often performed by clinicians manually. This process is time-consuming and usually affected by human factors. Hence, accurate and reliable automatic prostate zonal segmentation technology is highly desirable to liberate clinicians from tedious annotation work and prevent the problem of inter-observer variability.

Deep learning methods based on 3D convolutional neural networks (CNN) have been employed in some cutting-edge approaches for prostate zonal segmentation. These 3D CNNs have shown great performance under the conditions that massive voxel-level segmentation annotations of training data are available, and the training data share the same distribution with test data. However, these conditions may not always hold true in real-world scenarios where it is infeasible to collect voxel-level annotated training data for each medical center or imaging device.

SUMMARY OF THE INVENTION

According to one aspect of the present invention, the unsupervised domain adaptive segmentation network comprises a feature extractor configured for extracting features from a 3D MRI scan image; a decorrelation and whitening module configured for preforming decorrelation and whitening transformation on the extracted features to obtain whitened features; a domain-specific feature translation module configured for translating domain-specific features from a source domain into a target domain for adapting the unsupervised domain adaptive network to the target domain; and a classifier configured for projecting the whitened features into a zonal segmentation prediction.

According to another aspect of the present invention, a method for training the unsupervised domain adaptive segmentation network is provided. The training method comprises: preparing a labeled source domain training dataset from a source domain and an unlabeled target domain training dataset from the target domain; pre-training the unsupervised domain adaptive network on the labeled source domain dataset; and adapting the unsupervised domain adaptive network into the target domain with the labeled source domain training dataset and the unlabeled target domain training dataset.

At the beginning of the learning stage, the unsupervised domain adaptive segmentation network is unstable, thus, it is pre-trained from reliable labeled source data. With the domain-specific feature translation algorithm, source domain features are gradually and dynamically translated into the target domain to derive translated domain-specific features while class-specific features are kept unchanged to preserve the content information and semantic structure of prostate zones. The translated domain-specific features are devoid of source domain-specific traits but lies between the target and source data distribution. By using a mixing factor which is gradually increased in the learning process, more target domain patterns will be involved for optimization, and the learned network is thus able to gradually fit into the target domain data distribution.

By implementing the domain-specific feature translation module for transferring the knowledge learned from the labeled source domain data to unlabeled target domain data, data distribution discrepancy (also known as domain gap) between the source and target data can be narrowed. Therefore, the unsupervised domain adaptive segmentation network trained with labeled open-source prostate zonal segmentation dataset (i.e., source data) can perform in the target domain without performance degradation.

BRIEF DESCRIPTION OF THE DRAWINGS

Embodiments of the invention are described in more detail hereinafter with reference to the drawings, in which.

DETAILED DESCRIPTION

In the following description, exemplary embodiments of the present invention are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1:
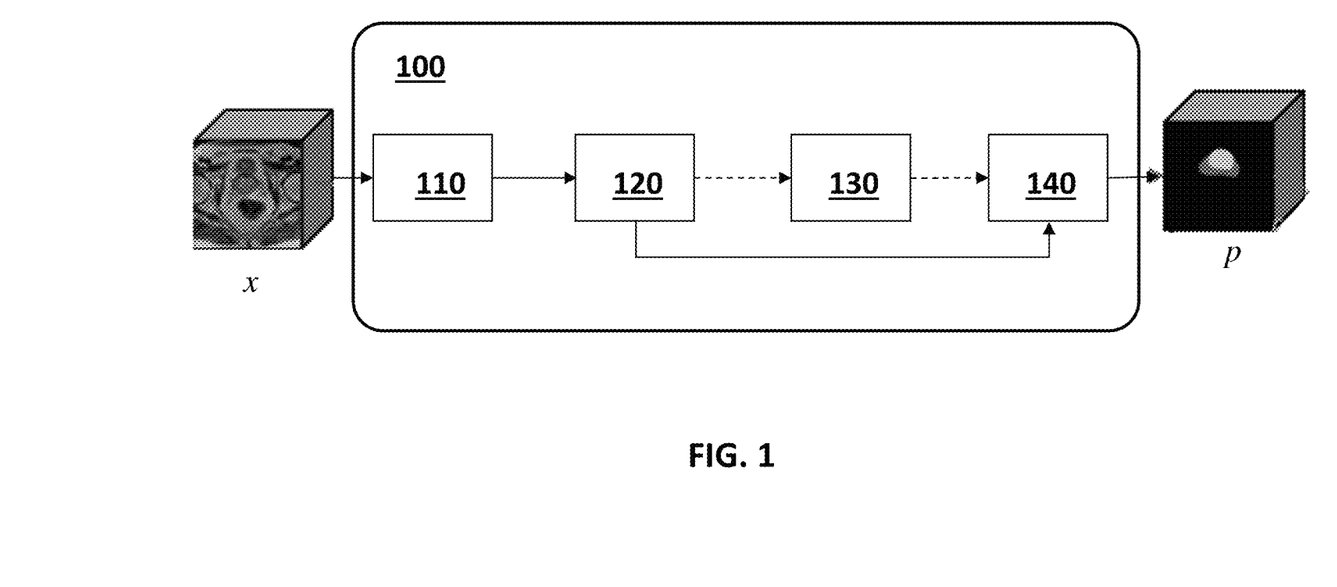
FIG. 1 depicts a block diagram of an unsupervised domain adaptive segmentation network according to one embodiment of the present invention.

FIG. 1 depicts a block diagram of an unsupervised domain adaptive segmentation network 100 for generating a zonal segmentation prediction p on a 3D MRI scan image x according to one embodiment of the present invention. The unsupervised domain adaptive segmentation network may be a 3D convolutional neural network, such as 3D UNet or a 3D VNet. As shown, the unsupervised domain adaptive segmentation network 100 may include a feature extractor 110 configured for extracting features from a 3D MRI scan image x, a decorrelation and whitening module 120 configured for preforming decorrelation and whitening transformation on the extracted features to obtain whitened features; a domain-specific feature translation module 130 configured for translating domain-specific features from a source domain into a target domain for adapting the unsupervised domain adaptive network to the target domain; and a classifier 140 configured for projecting the whitened features into a zonal segmentation prediction p.

Preferably, the decorrelation and whitening module 120 may be further configured for computing a domain covariance matrix of the extracted features; and utilizing the computed domain covariance matrix to project the extracted features into a spherical distribution to decorrelate and whiten the extracted features to obtain the whitened features.

As discussed in detail below, by implementing the domain-specific feature translation module 130, the unsupervised domain adaptive segmentation network 100 can be trained using a labeled training dataset in a source domain and an unlabeled training dataset in a target domain which is different from the source domain. The trained unsupervised domain adaptive segmentation network 100 can be used to generate a zonal segmentation prediction p on a 3D MRI scan x in the target domain.

Figure 2:
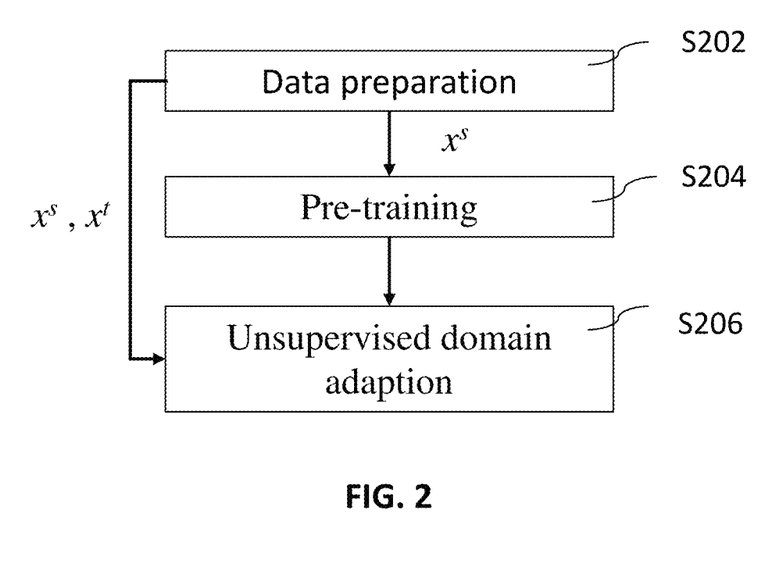
FIG. 2 depicts a framework for training the unsupervised domain adaptive segmentation network according to one embodiment of the present invention.

FIG. 2 depicts a framework for training the unsupervised domain adaptive segmentation network according to one embodiment of the present invention. The training process may be divided into three stages, namely, data preparation stage S202, pre-training stage S204 and unsupervised domain adaptation stage S206. In the data preparation stage S202, a labeled source domain training dataset $x^s$ and an unlabeled target domain training dataset $x^t$ may be prepared.

The labeled source domain training dataset $x^s$ may be any medical image segmentation dataset including 3D prostate MRI data equipped with prostate zone segmentation ground truths. For example, the labeled source domain dataset may be prepared by downloading data from some on-line databases such as Decathlon, NCI-ISBI13 and PROSTATEx. Decathlon is a comprehensive medical image segmentation dataset, including 32 prostate MRI scans obtained from 3T Siemens TIM, with annotations outlining the PZ and TZ. NCI-ISBI13 consists of 40 prostate MRI scans obtained from Radboud University Nijmegen Medical Centre with the imaging device of 1.5T Philips Achieva. Each MRI scan is equipped with the corresponding prostate zone segmentation ground truths. PROSTATEx is a publicly available 3D prostate MRI dataset obtained from two different types of Siemens 3T MR scanners, the MAGNETOM Trifo and Skyra. Notably, 98 MRI scans are with the corresponding voxel-wise segmentation annotations, indicating PZ and TZ of prostate.

The target domain training dataset $x^t$ may be prepared by routinely collecting data from some medical centers worldwide. For reference, 132 prostate cancer cases from the Stanford Hospital are collected and obtained under ethical Institutional Review Board (IRB) approval and used as the target domain training dataset. The target domain training dataset $x^t$ are randomly divided into three subsets: training, validation and test sets. For example, the target domain training dataset $x^t$ may be divided into training, validation and test sets in a proportion of 80%:10%:10%. The ground truths of validation and test sets are labeled by two experienced radiologists manually for evaluation purpose.

In the pre-training stage S204, the unsupervised domain adaptive segmentation network is pre-trained on the prepared source domain dataset $x^s$ (e.g., for 150 epochs) and optimized with an optimization algorithm such as stochastic gradient descent (SGD) to obtain basic ability of segmenting prostate zones.

In the unsupervised domain adaptation stage S206, which will be discussed in details below, the unsupervised domain adaptive segmentation network may be trained and adapted into the target domain with both the labeled source domain dataset $x^s$ and unlabeled target domain dataset $x^t$ (e.g., for 150 epochs) and optimized with an optimization algorithm such as SGD.

Figure 3:
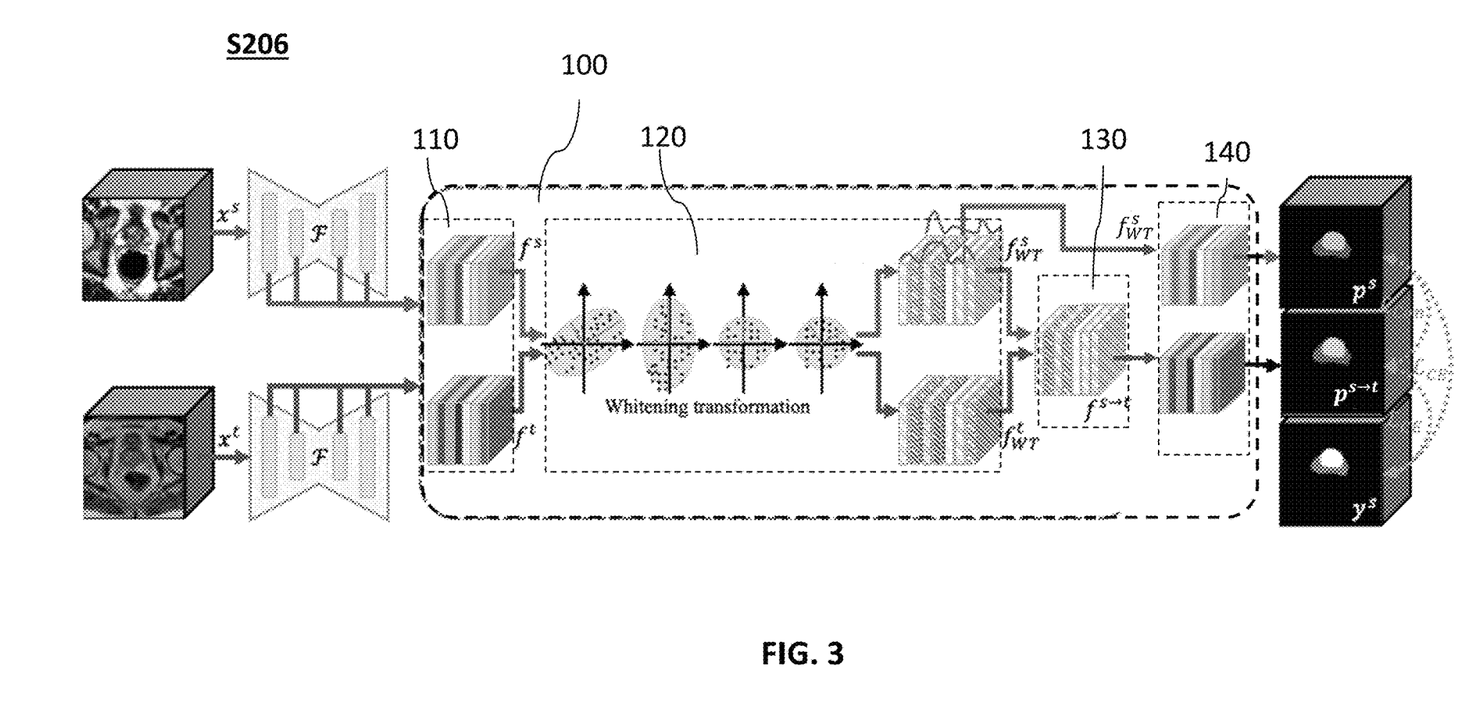
FIG. 3 depicts more details of the unsupervised domain adaptation stage for training the unsupervised domain adaptive segmentation network according to one embodiment of the present invention.

FIG. 3 depicts more details of the unsupervised domain adaptation stage S206 for training the unsupervised domain adaptive segmentation network 100 according to one embodiment of the present invention.

The feature extractor 110 may be configured and trained to extract source-domain features $f^s$ from the source domain training dataset $x^s$ and extract target-domain features $f^t$ from the target domain training dataset $x^t$.

The decorrelation and whitening module 120 may be configured and trained to preform decorrelation and whitening transformation on the extracted source-domain features $f^s$ and the extracted target-domain features $f^t$ to obtain whitened source-domain features $f_{WT}^s$ and whitened target-domain features $f_{WT}^t$.

More specifically, the decorrelation and whitening module 120 may be configured and trained to: compute domain-common covariance matrices of the extracted source-domain features $f^s$ and the extracted target-domain features $f^t$; and utilize the computed domain-common covariance matrices to project the extracted source-domain features $f^s$ and the extracted target-domain features $f^t$ into a common spherical distribution to decorrelate and whiten the extracted source-domain features $f^s$ and the extracted target-domain features $f^t$ to obtain the whitened source-domain features $f_{WT}^s$ and whitened target-domain features $f_{WT}^t$.

The domain-specific feature translation module 130 may be configured and trained to translate domain specific features in the whitened source-domain features $f_{WT}^s$ into the target domain to obtain translated domain-specific features $f^{s \to t}$.

More specifically, the domain-specific feature translation module 130 may be configured and trained to derive a source-domain variance for each of the whitened source-domain features $f_{WT}^s$ and determine whether each of the whitened source-domain specific features $f_{WT}^s$ is domain-specific or class-specific based on its corresponding source-domain variance. In particular, the derived source-domain variance may be compared against a threshold. If the derived source-domain variance is greater than the threshold, the corresponding whitened source-domain specific feature is determined to be domain-specific.

The domain-specific feature translation module 130 may further be configured and trained to derive a target-domain variance for each of the whitened target-domain features $f_{WT}^t$ and determine whether each of the whitened target-domain features $f_{WT}^t$ is domain-specific or class-specific based on its corresponding target-domain variance. In particular, the derived target-domain variance may be compared against a threshold. If the derived target-domain variance is greater than the threshold, the corresponding whitened target-domain specific feature is determined to be domain-specific.

The domain-specific feature translation module 130 may further be configured and trained to perform a plurality of iterations to mix source domain-specific features (i.e., activations with top-d percentile of the derived source-domain variance) in the whitened source-domain features $f_{WT}^s$ with corresponding target domain-specific features in the whitened target-domain features $f_{WT}^t$. Preferably, the source and target domain-specific features are mixed with a mixing factor $\lambda$ which is gradually increased over the plurality of iterations so as to progressively translate the whitened source-domain features $f_{W_t}^s$ into the target domain.

The translated domain-specific features $f^{s \to t}$ may then be formulated by:

$$f^{s \to t} = \lambda \times f_{WT}^s + (1-\lambda) \times \phi_t(f_{WT}^s, f_{WT}^t),$$

where $\phi_t$ is the feature translation operator that replaces the domain-specific features in the whitened source-domain features $f_{WT}^s$, with the corresponding features in the whitened target-domain features $f_{WT}^t$.

By way of example, in a t-th iteration, the mixing factor $\lambda$ may be given by:

$$\lambda = \min(t/T \times \lambda_0, 1),$$

where T is the total number of iterations to be performed, and $\lambda_0$ is a hyper-parameter.

The classifier 140 may be configured and trained to project the whitened source-domain features $f_{WT}^s$ and translated domain-specific features $f^{s \to t}$ into a source-domain zonal segmentation prediction $p^s$ and a translated domain-specific zonal segmentation prediction $p^{s \to t}$, respectively.

The unsupervised domain adaptive segmentation network 100 may be optimized by constraining the prediction $p^s$ under a source-domain specific cross-entropy loss $\mathcal{L}_{CE}^s$ and constraining the prediction $p^{s \to t}$ under a translated domain-specific cross-entropy loss $\mathcal{L}_{CE}^{s \to t}$.

Preferably, the source-domain specific cross-entropy loss $\mathcal{L}_{CE}^s$ and the translated domain-specific cross-entropy loss $\mathcal{L}_{CE}^{s \to t}$ are given by:

$$\mathcal{L}_{CE}^s = -\Sigma y^s \log p^s \text{ and}$$

$$\mathcal{L}_{CE}^{s \to t} = -\Sigma y^s \log p^{s \to t}, \text{respectively,}$$

where $y^s$ is prostate zone segmentation ground truths of the source domain data.

The unsupervised domain adaptive segmentation network 100 may be further adapted to fit into the target domain by enforcing consistency between the source-domain zonal segmentation prediction $p^s$ and the translated domain-specific zonal segmentation prediction $p^{s \to t}$ under a consistency regularization loss $\mathcal{L}_{Con}$.

The consistency regularization loss $\mathcal{L}_{Con}$ can be any suitable loss functions for quantifying difference between probability distributions, including but not limited to, Kullback-Leibler (KL) divergence, dice loss, mean squared error (MSE) loss, etc. For example, the consistency regularization loss $\mathcal{L}_{Con}$ may be a KL divergence function defined as:

$$\mathcal{L}_{Con} = \sum p^s \log \frac{p^s}{p^{s \to t}}.$$

Figure 4:
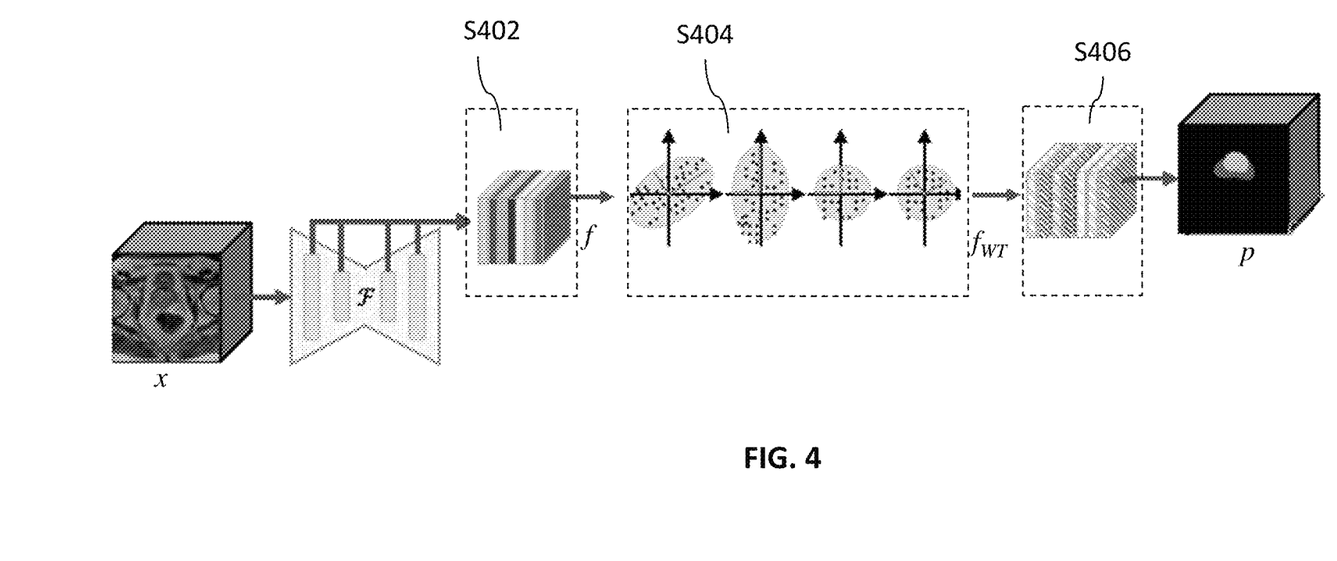
FIG. 4 depicts a workflow of using the trained unsupervised domain adaptive segmentation network to generate a zonal segmentation prediction on a 3D MRI scan image in a target domain.

FIG. 4 depicts a workflow of using the trained unsupervised domain adaptive segmentation network to generate a zonal segmentation prediction p on a 3D MRI scan image x in a target domain. As shown, the method may include: a feature extraction stage S402; a decorrelation and whitening transformation stage S404; and a segmentation stage S406.

The feature extraction S402 stage may include extracting, by a feature extractor, features f from the 3D MRI scan image x.

The decorrelation and whitening transformation stage S404 may include preforming decorrelation and whitening transformation on the extracted features f to obtain whitened features $f_{WT}$. More specifically, the decorrelation and whitening transformation stage S404 may include: computing a domain covariance matrix of the extracted features f; and utilizing the computed domain covariance matrix to project the extracted features f into a spherical distribution to decorrelate and whiten the extracted features f to obtain the whitened features $f_{WT}$.

The segmentation stage S406 may include projecting the whitened features $f_{WT}$ into the zonal segmentation prediction p.

Figure 5:
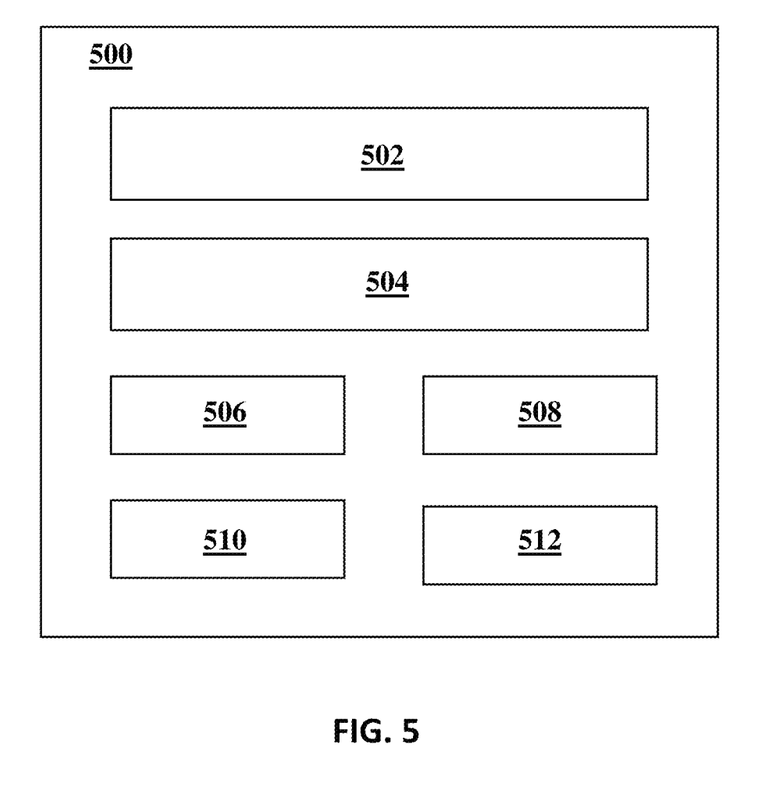
FIG. 5 depicts a block diagram of an exemplary system for training and deploying an unsupervised domain adaptive segmentation network according to one embodiment of the present invention.

FIG. 5 depicts a block diagram of an exemplary system 500 for training and deploying an unsupervised domain adaptive segmentation network according to one embodiment of the present invention. The system 500 may include at least one receiving module 502 configured for receiving or recording 3D MRI scans of a prostate of a patient.

The system 500 may further include a processor 504 which may be a CPU, an MCU, application specific integrated circuits (ASIC), field programmable gate arrays (FPGA) or any suitable programmable logic devices configured or programmed to be a processor for training and deploying the unsupervised domain adaptive segmentation network according to the teachings of the present disclosure.

The device 500 may further include a memory unit 506 which may include a volatile memory unit (such as RAM), a non-volatile unit (such as ROM, EPROM, EEPROM and flash memory) or both, or any type of media or devices suitable for storing instructions, codes, and/or data.

Preferably, the system 500 may further include one or more input devices 504 such as a keyboard, a mouse, a stylus, a microphone, a tactile input device (e.g., touch sensitive screen) and/or a video input device (e.g., camera). The system 500 may further include one or more output devices 510 such as one or more displays, speakers and/or disk drives. The displays may be a liquid crystal display, a light emitting display or any other suitable display that may or may not be touch sensitive.

The system 500 may also preferably include a communication module 512 for establishing one or more communication links (not shown) with one or more other computing devices such as a server, personal computers, terminals, wireless or handheld computing devices. The communication module 512 may be a modem, a Network Interface Card (NIC), an integrated network interface, a radio frequency transceiver, an optical port, an infrared port, a USB connection, or other interfaces. The communication links may be wired or wireless for communicating commands, instructions, information and/or data.

Preferably, the receiving module 502, the processing unit 504, the memory unit 506, and optionally the input devices 504, the output devices 510, the communication module 512 are connected with each other through a bus, a Peripheral Component Interconnect (PCI) such as PCI Express, a Universal Serial Bus (USB), and/or an optical bus structure. In one embodiment, some of these components may be connected through a network such as the Internet or a cloud computing network. A person skilled in the art would appreciate that the system 500 shown in FIG. 5 is merely exemplary, and that different systems 500 may have different configurations and still be applicable in the invention.

The foregoing description of the present invention has been provided for the purposes of illustration and description. It is not intended to be exhaustive or to limit the invention to the precise forms disclosed. Many modifications and variations will be apparent to the practitioner skilled in the art.

The apparatuses and the methods in accordance to embodiments disclosed herein may be implemented using computing devices, computer processors, or electronic circuitries and other programmable logic devices configured or programmed according to the teachings of the present disclosure. Computer instructions or software codes running in the computing devices, computer processors, or programmable logic devices can readily be prepared by practitioners skilled in the software or electronic art based on the teachings of the present disclosure.

All or portions of the methods in accordance to the embodiments may be executed in one or more computing devices including server computers, personal computers, laptop computers, mobile computing devices such as smartphones and tablet computers.

The embodiments were chosen and described in order to best explain the principles of the invention and its practical application, thereby enabling others skilled in the art to understand the invention for various embodiments and with various modifications that are suited to the particular use contemplated.

What is claimed is:

1. A method for training an unsupervised domain adaptive network to perform prostate zonal segmentation in a target domain, the unsupervised domain adaptive network comprises a feature extractor, a decorrelation and whitening module, a domain-specific feature translation module and a classifier, the method comprising:

preparing a labeled source domain training dataset from a source domain and an unlabeled target domain training dataset from the target domain;

pre-training the unsupervised domain adaptive network on the labeled source domain dataset; and adapting the unsupervised domain adaptive network into the target domain with the labeled source domain training dataset and the unlabeled target domain training dataset;

wherein adapting the unsupervised domain adaptive network into the target domain includes:

extracting, by the feature extractor, a plurality of source-domain features from the source domain training dataset and a plurality of target-domain features from the target domain training dataset;

performing by the decorrelation and whitening module, decorrelation and whitening transformation on the plurality of extracted source-domain features and the plurality of extracted target-domain features to obtain a plurality of whitened source-domain features whitened and a plurality of whitened target-domain features;

translating, by the domain-specific feature translation module, a plurality of domain specific features in the plurality of whitened source-domain features into the target domain to obtain a plurality of translated domain-specific features;

projecting, by the classifier, the plurality of whitened source-do features and the plurality of translated domain-specific features into a source-domain zonal segmentation prediction and a translated domain-specific zonal segmentation prediction, respectively; and enforcing consistency between the source-domain zonal segmentation prediction and the translated domain-specific zonal segmentation prediction under a consistency regularization loss; and wherein the translation of the plurality of domain specific features in the plurality of whitened source-domain features into the target domain comprises:

deriving a corresponding source-domain variance for each of the plurality of whitened source-domain features and determining whether the whitened source-domain feature is domain-specific or class-specific based on the corresponding source-domain variance;

deriving a corresponding target-domain variance for each of the plurality of whitened target-domain features and determining whether the whitened target-domain specific feature is domain-specific or class-specific based on the corresponding target-domain variance; and performing a plurality of iterations to mix a plurality of source domain-specific features in the whitened source domain features with a plurality of corresponding target domain-specific features in the whitened target-domain features.

2. The method according to claim 1, wherein the decorrelation and whitening transformation comprises:

computing a plurality of domain-common covariance matrices of the plurality of extracted source-domain features and the plurality of extracted target-domain features; and utilizing the plurality of computed domain-common covariance matrices to project the plurality of extracted source-domain features and the plurality of extracted target-domain features into a common spherical distribution to decorrelate and whiten the source-domain features and the target-domain features to obtain the plurality of whitened source-domain features and the plurality of whitened target-domain features.

3. The method according to claim 1, wherein the plurality of source domain-specific features and the plurality of target domain-specific features are mixed with a mixing factor $\lambda$ which is gradually increased over the plurality of iterations so as to progressively translate the whitened source-domain features into the target domain.

4. The method according to claim 3, wherein the mixing factor $\lambda$ in a t-th iteration is given by:

$$\lambda = \min(t/T \times \lambda_0, 1),$$

where T is the total number of iterations to be performed and $\lambda_0$ is a hyper-parameter.

5. The method according to claim 4, wherein the translated domain-specific features are formulated by:

$$f^{s \to t} = \lambda \times f_{WT}^s + (1-\lambda) \times \phi_t(f_{WT}^s, f_{WT}^t),$$

where $f^{s \to t}$ denotes the translated domain-specific features, $f_{WT}^s$ denotes the whitened source domain features, $f_{WT}^t$ denotes the whitened target-domain features, $\phi_t$ is the feature translation operator that replaces the domain-specific features in the whitened source-domain features with the corresponding features in whitened target-domain features.

6. The method according to claim 5, wherein the consistency regularization loss is given by:

$$\mathcal{L}_{Con} = \sum p^s \log \frac{p^s}{p^{s \to t}},$$

where $\mathcal{L}_{Con}$ denotes the consistency regularization loss, $p^s$ is the source-domain zonal segmentation prediction and $p^{s \to t}$ is the translated domain-specific zonal segmentation prediction.

7. The method according to claim 1, wherein:

the labeled source domain dataset is a medical image segmentation dataset including a plurality of 3D prostate magnetic resonance imaging (MRI) data, each equipped with corresponding prostate zone segmentation ground truths; and the unlabeled target domain dataset includes prostate cancer MRI data collected from medical centers.

\* \* \* \* \*